US012788760B2

(12) United States Patent
Spargo et al.

(10) Patent No.: US 12,788,760 B2
(45) Date of Patent: Nov. 10, 2026

(54) LIQUID PHARMACEUTICAL COMPOSITION COMPRISING ENSIFENTRINE AND GLYCOPYRROLATE

(71) Applicant: VERONA PHARMA LIMITED, London (GB)

(72) Inventors: Peter Lionel Spargo, Canterbury Kent (GB); Phillip Andrew Haywood, Hertfordshire (GB); Edward James French, Canterbury Kent (GB)

(73) Assignee: VERONA PHARMA LIMITED, London (GB)

( * ) Notice: Subject to any disclaimer, the term of this patent is extended or adjusted under 35 U.S.C. 154(b) by 359 days.

(21) Appl. No.: 17/904,816

(22) PCT Filed: Feb. 26, 2021

(86) PCT No.: PCT/GB2021/050496

§ 371 (c)(1),
(2) Date: Aug. 23, 2022

(87) PCT Pub. No.: WO2021/171034

PCT Pub. Date: Sep. 2, 2021

(65) Prior Publication Data

US 2023/0112220 A1 Apr. 13, 2023

(30) Foreign Application Priority Data

Feb. 27, 2020 (GB) ..................................... 2002786

(51) Int. Cl.
*A61K 31/519* (2006.01)
*A61K 9/00* (2006.01)
*A61K 31/40* (2006.01)
*A61K 47/02* (2006.01)
*A61K 47/12* (2006.01)

(52) U.S. Cl.
CPC .......... *A61K 31/519* (2013.01); *A61K 9/0078* (2013.01); *A61K 31/40* (2013.01); *A61K 47/02* (2013.01); *A61K 47/12* (2013.01)

(58) Field of Classification Search
CPC ............................. A61K 9/0078; A61P 11/00
See application file for complete search history.

(56) References Cited

U.S. PATENT DOCUMENTS 6,794,391 B2 9/2004 Oxford et al.
7,105,663 B2 9/2006 Oxford et al.
7,378,424 B2 5/2008 Oxford et al.
8,242,127 B2 8/2012 Oxford et al.
9,700,558 B2 7/2017 Walker et al.
9,717,732 B2 8/2017 Walker et al.
9,956,171 B2 5/2018 Spargo et al.
10,463,665 B2 11/2019 Spargo et al.
10,710,998 B2 7/2020 Spargo
10,864,213 B2 12/2020 Abbott-Banner et al.
10,945,950 B2 3/2021 Spargo et al.
11,491,155 B2 11/2022 Spargo et al.
11,759,467 B2 9/2023 Abbott-Banner et al.
12,168,011 B2 12/2024 Spargo et al.
12,194,045 B1 1/2025 Spargo et al.
12,251,384 B1 3/2025 Spargo et al.
12,409,180 B2 9/2025 Spargo et al.
2003/0036542 A1 2/2003 Oxford et al.
2004/0171828 A1 9/2004 Oxford et al.
2004/0176353 A1 9/2004 Oxford et al.
2008/0206163 A1 8/2008 Oxford et al.
2009/0215734 A1 8/2009 Gerhart
2012/0302533 A1 11/2012 Oxford et al.
2013/0225616 A1 8/2013 Walker et al.
2016/0000790 A1* 1/2016 Walker .................... A61P 27/02 128/200.23
2017/0112839 A1 4/2017 Abbott-Banner et al.
2017/0239178 A1* 8/2017 Spargo .................... A61P 37/08
2017/0266190 A1 9/2017 Walker et al.
2018/0369139 A1 12/2018 Spargo et al.
2019/0330206 A1 10/2019 Spargo
2020/0016158 A1 1/2020 Spargo et al.
2021/0106585 A1 4/2021 Abbott-Banner et al.
2021/0379053 A1 12/2021 Spargo et al.
2022/0265549 A1 8/2022 Spargo et al.
2024/0165023 A1 5/2024 Spargo et al.
2024/0165054 A1 5/2024 Rheault et al.
2024/0165055 A1 5/2024 Rheault et al.
2024/0165117 A1 5/2024 Spargo et al.
2024/0173327 A1 5/2024 Rickard et al.
2024/0382489 A1 11/2024 Spargo et al.
2025/0049781 A1 2/2025 Spargo et al.
2025/0170135 A1 5/2025 Spargo et al.
2025/0249006 A1 8/2025 Rheault
2025/0249007 A1 8/2025 Spargo et al.
2025/0249008 A1 8/2025 Spargo et al.
2025/0319090 A1 10/2025 Spargo et al.

FOREIGN PATENT DOCUMENTS

WO 2006100453 A1 9/2006
WO 2012020016 A1 2/2012
WO 2014140647 A1 9/2014
WO 2014140648 A1 9/2014
WO 2015173551 A1 11/2015
WO 2016042313 A1 3/2016
(Continued)

OTHER PUBLICATIONS

Clinical Pharmacology Review Glycopyrrolate Inhalation Powder He et al. Dec. 29, 2014 Center for Drug Evaluation and Research (Year: 2014).*

(Continued)

*Primary Examiner* — Jeffrey S Lundgren
*Assistant Examiner* — Eric Tran
(74) *Attorney, Agent, or Firm* — MH2 Technology Law Group, LLP

(57) ABSTRACT

The present invention relates to a liquid pharmaceutical composition suitable for administration by inhalation comprising: (i) ensifentrine particles; (ii) glycopyrrolate; and (iii) a diluent, which diluent comprises water, wherein: the glycopyrrolate is dissolved in the diluent; the concentration of glycopyrrolate is less than or equal to 5.0 mg/mL; and the pH of the liquid pharmaceutical composition is from 3.0 to 6.0. The invention also relates to a nebuliser comprising the liquid pharmaceutical composition.

21 Claims, No Drawings

(56) References Cited

FOREIGN PATENT DOCUMENTS

| | | | |
|---|---|---|---|
| WO | 2016128742 | A1 | 8/2016 |
| WO | 2018020249 | A1 | 2/2018 |
| WO | 2020074894 | A1 | 4/2020 |
| WO | 2000058308 | A1 | 10/2020 |
| WO | 2021028679 | A1 | 2/2021 |

OTHER PUBLICATIONS

Almeida et al., "Topical and systemic anticholinergic for treating hyperhidrosis", Shanghai Chest, 2019, vol. 3, 6 pages. (found online, found on the Internet: https://shc.amegroups.org/article/view/5233/pdf).
Abbott-Banner et al., "Dual PDE3/4 and PDE4 inhibitors: novel treatments for COPD and other inflammatory airway diseases", Basic Clin Pharmacol Toxicol., May 2014, vol. 114, No. 5, pp. 365-376. doi: 10.11n/bcpt.12209. Epub Mar. 6, 2014.
Bochkov et al., "Factors affecting biological accessibility medicinal drugs", Pharmacokinetics and pharmacodynamics, 2016, 1, 18 pages, with machine English Translation. (found online, found on the Internet: https://cyberienmka.m/article/n/faktory-vliyayuschie-na-biologicheskuyu-dostupnostlekarstvennyh-preparatov/viewer).
Myrdal et al., "Advances in metered dose inhaler technology: formulation development", AAPS PharmSciTech., Apr. 2014., vol. 15, No. 2, pp. 434-455. doi: 10.1208/s12249-013-0063-x.
English translation of Office Action dated Jun. 26, 2024 for corresponding Russian Application No. 2022123005/04, 9 pages.
European Patent Office, Decision to Grant in European Application No. 21709782.3, 46 pages, mailed Sep. 12, 2023.
Sindel, Ulrike (Authorized Officer), International Search Report and Written Opinion dated May 3, 2021 for International Application No. PCT/GB2021/050496, 11 pages.
Calzetta, Luigino et al., "Pharmacological characterization of the interaction between the dual phosphodiesterase (PDE) 3/4 inhibitor RPL554 and glycopyrronium on human isolated bronchi and small airways", Pulmonary Pharmacology & Therapeutics, vol. 32, Jan. 1, 2015, pp. 15-23.
Calzetta, Luigino et al., "Effect of the Mixed Phosphodiesterase 3/4 Inhibitor RPL554 on Human Isolated Bronchial Smooth Muscle Tone", Journal of Pharmacology and Experimental Therapeutics, vol. 346, No. 3, Jun. 13, 2013, pp. 414-423.

* cited by examiner

LIQUID PHARMACEUTICAL COMPOSITION COMPRISING ENSIFENTRINE AND GLYCOPYRROLATE

CROSS-REFERENCE TO RELATED APPLICATIONS

This application is a U.S. National Stage application of PCT/GB2021/050496 filed 26 Feb. 2021, which claims priority to Application No. GB2002786.8 filed 27 Feb. 2020, the entire disclosures of which are herein incorporated by reference.

FIELD OF THE INVENTION

The present invention relates to an inhalable liquid pharmaceutical composition comprising ensifentrine and glycopyrrolate. The invention also relates to a nebuliser comprising the liquid pharmaceutical composition.

BACKGROUND OF THE INVENTION

Ensifentrine (N-(2-{(2E)-9,10-dimethoxy-4-oxo-2-[(2,4,6-trimethylphenyl)imino]-6,7-dihydro-2H-pyrimido[6,1-a]isoquinolin-3(4H)-yl}ethyl)urea; also known as RPL554) is a dual PDE3/PDE4 inhibitor and is described in WO 00/58308 A1.

As a combined PDE3/PDE4 inhibitor, ensifentrine has both bronchodilatory and anti-inflammatory activity and is useful in the treatment of respiratory disorders such as asthma and chronic obstructive pulmonary disease (COPD). The structure of ensifentrine is shown below.

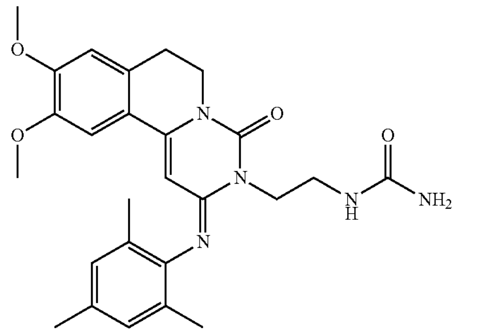 [SMILES: COc1cc2c(cc1OC)-c1c/c(=N\c3c(C)cc(C)cc3C)n(CCNC(N)=O)c(=O)n1CC2]

WO 2016/042313 A describes formulations of ensifentrine as a suspension of particles in an aqueous diluent.

Ensifentrine may be used in combination with the muscarinic receptor antagonist glycopyrrolate. As used herein "glycopyrrolate" means a salt comprising the cation glycopyrronium. Glycopyrronium has the formula (1,1-dimethylpyrrolidin-1-ium-3-yl) 2-cyclopentyl-2-hydroxy-2-phenylacetate. The structure of glycopyrronium is shown below.

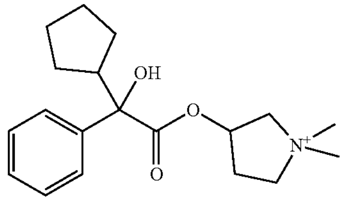 [SMILES: C[N+]1(C)CCC(OC(=O)C(O)(c2ccccc2)C2CCCC2)C1]

A combination of ensifentrine and glycopyrrolate useful for treating respiratory disorders is described in WO 2014/140648 A.

The formulation of pharmaceutical compounds is complex and unpredictable. This is particularly the case for liquid pharmaceutical compositions for administration by inhalation. For instance, such inhalable liquid pharmaceutical compositions must be sufficiently stable so that a suitably consistent dose is delivered during inhalation, even after storage for a period of time. The difficulties associated with preparation of an inhalable pharmaceutical composition are compounded when that composition comprises two active agents, for instance as for the combination of ensifentrine and glycopyrrolate. For such combination formulations, stability of both pharmaceutical compounds must be controlled.

There is a need to develop a liquid pharmaceutical composition comprising ensifentrine and glycopyrrolate in which both compounds are stable. It is also desirable to prepare a liquid pharmaceutical composition which is suitable for administration by inhalation.

SUMMARY OF THE INVENTION

It is a surprising finding of the present invention that a pharmaceutical composition in which both ensifentrine and glycopyrrolate are stable can be produced by formulating ensifentrine as a suspension of particles and glycopyrrolate as a solution in an aqueous diluent at a low pH and in which the concentration of glycopyrrolate is low relative to the concentration of ensifentrine. This specific formulation in which ensifentrine is suspended and glycopyrrolate is dissolved has been shown to be stable with respect to chemical degradation of both active agents after storage for at least three months.

The invention accordingly provides a liquid pharmaceutical composition suitable for administration by inhalation comprising: (i) ensifentrine particles; (ii) glycopyrrolate; and (iii) a diluent, which diluent comprises water, wherein: the glycopyrrolate is dissolved in the diluent; the concentration of glycopyrrolate is less than or equal to 5.0 mg/mL; and the pH of the liquid pharmaceutical composition is from 3.0 to 6.0.

The invention also provides a nebuliser comprising a liquid pharmaceutical composition according to the invention.

Further provided by the invention is a liquid pharmaceutical composition according to the invention for use in the treatment of the human or animal body.

DETAILED DESCRIPTION OF THE INVENTION

The liquid pharmaceutical composition comprises glycopyrrolate. Glycopyrrolate is typically present in the liquid pharmaceutical composition as a pharmaceutically acceptable salt of glycopyrronium. Glycopyrrolate is typically the bromide salt, glycopyrronium bromide, but other pharmaceutically acceptable salts of glycopyrronium may be used, for instance glycopyrronium chloride. The glycopyrrolate is preferably glycopyrronium bromide.

The glycopyrrolate is dissolved in the diluent. Accordingly, of the total mass of glycopyrrolate present in the liquid pharmaceutical composition, at least some (for instance at least 50% by weight) is dissolved in the diluent. Typically, substantially all of the glycopyrrolate is dissolved in the diluent. For example, at least 99.0% by weight of the glycopyrrolate may be dissolved in the diluent, relative to the total mass of glycopyrrolate in the liquid pharmaceutical composition. The term "dissolved" takes its normal meaning in the art, for instance that the glycopyrrolate is in solution in the diluent and cannot be recovered by standard filtration.

The pharmaceutical composition is a liquid pharmaceutical composition and, as such, is liquid under ambient conditions (for instance at temperatures from 10 to 40° C.).

The pH of the liquid pharmaceutical composition is from 3.0 to 6.0. Typically, the pH of the liquid pharmaceutical composition is from 3.5 to 5.0. For instance, the pH of the liquid pharmaceutical composition may be from 4.3 to 4.7. The pH of the liquid pharmaceutical composition may be from 3.5 to 4.5, for instance from 3.8 to 4.2.

The pH of the liquid pharmaceutical composition is typically the pH as measured at a temperature of 20° C. The pH of the liquid pharmaceutical composition may be measured by any suitable technique. For instance, the pH may be as measured using a potentiometric pH meter.

The liquid pharmaceutical composition typically further comprises a buffer. The buffer can be used to control the pH of the liquid pharmaceutical composition. A buffer typically comprises a weak acid and its conjugate base. Examples of buffers include a citrate buffer, a phosphate buffer, an acetate buffer, and a bicarbonate buffer.

Preferably, the buffer is a citrate buffer. A citrate buffer typically comprises citric acid and a citrate salt. For instance, the citrate buffer may comprise citric acid and trisodium citrate. The citric acid may be citric acid monohydrate. The trisodium citrate may be trisodium citrate dihydrate.

The concentration of the buffer is typically from 10.0 to 40.0 mg/m L. Preferably the buffer concentration is from 20.0 to 30.0 mg/mL. The concentration of the buffer includes both the acid and conjugate base components of the buffer.

The concentration of glycopyrrolate in the liquid pharmaceutical composition is less than or equal to 5.0 mg/m L. For instance, the concentration of glycopyrrolate may be from 0.001 to 5.0 mg/mL. Typically, the concentration of glycopyrrolate is from 0.01 mg/mL to 2.0 mg/mL, for instance from 0.01 to 1.0 mg/mL.

Preferably, the glycopyrrolate concentration is from 0.02 mg/mL to 0.25 mg/mL. For instance, the concentration of glycopyrrolate may be from 0.14 to 0.16 mg/m L. The concentration of glycopyrrolate may be from 0.02 to 0.03 mg/mL, for instance about 0.025 mg/mL (25 μg/mL).

The liquid pharmaceutical composition comprises ensifentrine particles. The ensifentrine particles comprise ensifentrine (i.e. ensifentrine free base) or a pharmaceutically acceptable salt thereof. Typically, the ensifentrine particles comprise ensifentrine. The ensifentrine particles typically comprise at least 90.0 wt % of ensifentrine or a pharmaceutically acceptable salt thereof, more preferably at least 95.0 wt %. The ensifentrine particles may consist essentially of ensifentrine or a pharmaceutically acceptable salt thereof, or may consist of ensifentrine or a pharmaceutically acceptable salt thereof. For instance, the ensifentrine particles may consist of ensifentrine free base.

A composition which consists essentially of a component typically comprises only that component and other components which do not materially affect the essential characteristics of the component of which the composition essentially consists. A composition consisting essentially of a component may comprise at least 99.5 wt % of that component relative to the total weight of the composition.

The ensifentrine particles in the liquid pharmaceutical composition are typically suspended in the diluent. The liquid pharmaceutical composition accordingly typically comprises a suspension of the ensifentrine particles. It may also be the case that some or all of the ensifentrine particles in the liquid pharmaceutical composition have settled to the bottom of a receptacle containing the liquid pharmaceutical composition, for instance after storage for a period of time. The ensifentrine particles may be re-suspended in any suitable way, for instance by agitation of the liquid pharmaceutical composition.

The weight ratio of ensifentrine:glycopyrrolate in the liquid pharmaceutical composition may be from 1:5 to 200:1. For instance, for each 1 gram of ensifentrine in the composition, there may be from 0.005 to 5.0 grams of glycopyrrolate. Typically, the total concentration of ensifentrine in the liquid pharmaceutical composition is greater than the total concentration of glycopyrrolate in the liquid pharmaceutical composition. Preferably, the weight ratio of ensifentrine:glycopyrrolate in the liquid pharmaceutical composition is from 5:1 to 150:1. The weight ratio of ensifentrine:glycopyrrolate in the liquid pharmaceutical composition may be from 15:1 to 120:1, for example from 8:1 to 12:1.

The concentration of ensifentrine particles in the liquid pharmaceutical composition can be any suitable concentration, for instance from 0.01 to 400 mg/m L. Typically, the concentration of ensifentrine particles is from 0.1 to 5.0 mg/mL. Preferably, the concentration of ensifentrine particles is from 0.1 to 2.5 mg/mL. For instance, the concentration of ensifentrine particles may be from 0.15 to 0.5 mg/mL or from 1.0 to 2.0 mg/mL.

The ensifentrine particles typically have a Dv50 of from 0.5 μm to 5.0 μm. The ensifentrine particles preferably have a Dv50 of from 1.0 μm to 2.0 μm. Typically, the Dv10 of the ensifentrine particles is from 0.2 μm to 1.0 μm and the Dv90 of the ensifentrine particles is from 2.5 μm to 6.0 μm. For instance, the Dv10 of the ensifentrine particles may be from 0.4 μm to 0.6 μm and the Dv90 of the ensifentrine particles may be from 2.8 μm to 3.8 μm.

Particle sizes are described herein by reference to the Dv50 value, which is the median particle size for a volume distribution. Thus, half the volume of the particles have diameters of less than the Dv50 value and half the volume of the particles have diameters of greater than the Dv50 value. This is a well-known manner in which to describe particle size distributions. The parameters of Dv10 and Dv90 may also be used to characterise a particle size distribution of a sample. 10% of the volume of particles have a diameter of less than the Dv10 value. 90% of the volume of the particles have a diameter of less than the Dv90 value.

The technique used to measure the Dv50 (and Dv10 and Dv90) values as stated herein is typically laser diffraction. The particle size distribution of the ensifentrine particles may be as measured by laser diffraction using a wet powder dispersion system. For instance, the particle size distribution can be measured by laser diffraction using a Malvern Spraytec in conjunction with a wet dispersion cell. Typically, the instrument parameters for the Malvern Spraytec are as follows:

particle—standard opaque particle;
refractive index Particle—1.50;
refractive index (imaginary)—0.50;
density of particle—1.00;
refractive index of dispersant—1.33;
controller unit—1000 RPM;
measurement type—timed;

initial sampling time—30 s;

obscuration—20%-30%;

dispersant—1% Polysorbate 20 in deionised water.

The ensifentrine particles may be produced by any pharmaceutically acceptable size reduction process or particle size controlled production process. For instance, the particles may be produced by spray-drying a solution of ensifentrine, by controlled crystallisation, or by size reduction of a solid form of ensifentrine, for example by air jet milling, mechanical micronisation or media milling.

The diluent comprises water. The diluent may for instance comprise water and a secondary solvent such as ethanol. Typically, the liquid pharmaceutical composition comprises at least 50% by weight of water based on the total weight of the liquid pharmaceutical composition. Preferably, the diluent is water and the liquid pharmaceutical composition comprises at least 80% by weight of the diluent based on the total weight of the liquid pharmaceutical composition. The diluent is typically sterile. The liquid pharmaceutical composition is typically sterile.

The liquid pharmaceutical composition typically further comprises a tonicity adjuster. Examples of tonicity adjusters include sodium chloride, potassium chloride, glucose, glycerine and mannitol. Preferably, the tonicity adjuster is sodium chloride.

The concentration of the tonicity adjuster is typically greater than or equal to 1.0 mg/mL (for instance from 1.0 to 50.0 mg/mL). Preferably, the tonicity adjuster concentration is from 4.0 to 20.0 mg/mL, more preferably from 6.0 to 12.0 mg/mL.

The liquid pharmaceutical composition typically further comprises one or more surfactants. The one or more surfactant may comprise a non-ionic surfactant, an anionic surfactant, a cationic surfactant, a zwitterionic surfactant or a mixture thereof. Typically, the one or more surfactants comprise a non-ionic surfactant.

Examples of surfactants include lecithin, oleic acid, polyoxyethylene glycol alkyl ethers (for instance PEG 300, PEG 600, PEG 1000, Brij 30, Brij 35, Brij 56, Brij 76 and Brij 97), polypropylene glycol (for instance PPG 2000), glucoside alkyl ethers, polyoxyethylene glycol octylphenol ethers, polyoxyethylene glycol alkylphenol ethers, glycerol alkyl esters, polyoxyethylene glycol sorbitan alkyl esters (polysorbates, for instance polysorbate 20, polysorbate 40, polysorbate 60 and polysorbate 80), sorbitan alkyl esters (for instance sorbitan monolaurate (Span 20), sorbitan monooleate (Span 80) and sorbitan trioleate (Span 85)), cocamide MEA, cocamide DEA, dodecyldimethylamine oxide, block copolymers of polyethylene glycol and polypropylene glycol (poloxamers), block copolymers of polyethylene glycol and polypropylene oxide (for instance Pluronic surfactants), polyvinyl pyrrolidone K25, polyvinyl alcohol, oligolactic acid, sodium dioctyl sulfosuccinate and polyethoxylated tallow amine (POEA).

Preferably, the one or more surfactants comprise a polysorbate and/or a sorbitan alkyl ester. The one or more surfactants may for instance comprise polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate) or polysorbate 80 (polyoxyethylene (20) sorbitan monooleate). The one or more surfactants may for instance comprise sorbitan monolaurate (Span 20), sorbitan monooleate (Span 80) or sorbitan trioleate (Span 85). Preferably, the liquid pharmaceutical composition comprises polysorbate 20 and/or sorbitan monolaurate (Span 20).

The liquid pharmaceutical composition may comprise two or more surfactants, or the liquid pharmaceutical composition may comprise a single surfactant. For instance the composition may comprise a single surfactant which is a polysorbate, for instance polysorbate 20. The composition may comprise two or more surfactants. For instance, the liquid pharmaceutical composition may comprise polysorbate 20 and sorbitan monolaurate (Span 20).

The total concentration of the one or more surfactants is typically from 0.01 to 2.0 mg/mL. Preferably, the total surfactant concentration is from 0.1 to 1.0 mg/mL. For instance, the total surfactant concentration in the liquid pharmaceutical composition may be from 0.25 to 0.75 mg/mL. The liquid pharmaceutical composition may for instance comprise a polysorbate at a concentration of from 0.1 to 1.0 mg/mL and optionally a sorbitan alkyl ester at a concentration of from 0.01 to 0.1 mg/m L.

The liquid pharmaceutical composition typically comprises:

(i) ensifentrine particles;
(ii) glycopyrrolate;
(iii) the diluent;
(iv) a polysorbate surfactant;
(v) a citrate buffer; and
(vi) sodium chloride.

For instance, the liquid pharmaceutical composition may comprise:

(i) from 0.1 to 2.5 mg/mL ensifentrine particles, optionally from 0.5 to 2.5 mg/mL ensifentrine particles;
(ii) from 0.01 mg/mL to 2.0 mg/mL glycopyrronium bromide;
(iii) water;
(iv) from 0.1 to 1.0 mg/mL polysorbate 20;
(v) from 5.0 to 15.0 mg/mL citric acid;
(vi) from 10.0 to 20.0 mg/mL trisodium citrate; and
(vii) from 5.0 to 15.0 mg/mL sodium chloride.

The liquid pharmaceutical composition may for instance comprise:

(i) ensifentrine particles;
(ii) glycopyrrolate;
(iii) the diluent;
(iv) a polysorbate surfactant;
(v) a sorbitan alkyl ester surfactant;
(vi) a citrate buffer; and
(vii) sodium chloride.

For example, the liquid pharmaceutical composition may comprise:

(i) from 0.1 to 2.5 mg/mL ensifentrine particles, optionally from 0.5 to 2.5 mg/mL ensifentrine particles;
(ii) from 0.01 mg/mL to 2.0 mg/mL glycopyrronium bromide;
(iii) water;
(iv) from 0.1 to 1.0 mg/mL polysorbate 20;
(v) from 0.01 to 0.1 mg/mL sorbitan monolaurate;
(vi) from 5.0 to 15.0 mg/mL citric acid;
(vii) from 10.0 to 20.0 mg/mL trisodium citrate; and
(viii) from 5.0 to 15.0 mg/mL sodium chloride.

The liquid pharmaceutical composition may consist, or consist essentially of, components (i) to (vi), components (i) to (vii) or components (i) to (viii).

The liquid pharmaceutical composition is advantageously stable. In particular, the liquid pharmaceutical composition is typically stable with respect to chemical degradation of ensifentrine and glycopyrrolate for at least one month when stored at a temperature of 25° C. and a relative humidity of 60%. The liquid pharmaceutical composition may for instance be stable under these conditions for at least three months.

The liquid pharmaceutical composition may be produced by standard formulation methods. The liquid pharmaceutical composition is typically produced by a method comprising dissolving glycopyrrolate in the diluent to produce a solution of glycopyrrolate and mixing the ensifentrine particles with the solution of glycopyrrolate to produce a suspension of ensifentrine particles. The liquid pharmaceutical composition may alternatively be produced by a method comprising mixing the ensifentrine particles with the diluent to produce a suspension of ensifentrine particles and then dissolving the glycopyrrolate in the suspension.

The liquid pharmaceutical composition is suitable for administration by inhalation. Typically, the liquid pharmaceutical composition is suitable for administration by a nebuliser.

The invention provides a nebuliser comprising a liquid pharmaceutical composition according to the invention. The nebuliser is typically loaded with the liquid pharmaceutical composition. The nebuliser typically comprises from about 1.0 mL to about 200 mL, more typically from 1.0 mL to 20 mL of the liquid pharmaceutical composition. The nebuliser preferably comprises from 2.0 mL to 5.0 mL of the liquid pharmaceutical composition, for instance about 2.5 mL.

Nebulisers aerosolise a liquid pharmaceutical composition into an aerosol that is inhaled into a subject's respiratory tract. Examples of nebulisers include a soft mist nebuliser, a vibrating mesh nebuliser, a jet nebuliser and an ultrasonic wave nebuliser. Suitable nebuliser devices include the Philips I-neb™ (Philips), the Philips SideStream (Philips), the AeroNeb® (Philips), the Philips InnoSpire Go (Philips), the Pari LC Sprint (Pari GmbH), the AERxR™ Pulmonary Delivery System (Aradigm Corp) and the Pari LC Plus Reusable Nebuliser (Pari GmbH).

Ensifentrine is useful in the treatment of respiratory diseases and inflammatory diseases. Glycopyrrolate is useful in the treatment of respiratory diseases. Ensifentrine and glycopyrrolate have been found to interact synergistically in causing relaxation of bronchial smooth muscle. The invention provides a liquid pharmaceutical composition according to the invention for use in the treatment of the human or animal body. Typically, the liquid pharmaceutical composition is administered by inhalation.

The liquid pharmaceutical composition is typically for use in the treatment or prevention of a disease or condition selected from chronic obstructive pulmonary disease (COPD), asthma, allergic asthma, hay fever, allergic rhinitis, bronchitis, emphysema, bronchiectasis, adult respiratory distress syndrome (ARDS), steroid resistant asthma, severe asthma, paediatric asthma, cystic fibrosis, lung fibrosis, pulmonary fibrosis, interstitial lung disease, a skin disorder, atopic dermatitis, psoriasis, ocular inflammation, cerebral ischaemia, an inflammatory disease and an auto-immune disease. Preferably the disease or condition is COPD or asthma. More preferably, the disease or condition is chronic obstructive pulmonary disease (COPD).

An effective amount of ensifentrine is typically from about 0.001 mg/kg to 50 mg/kg for a single dose, for instance from 0.01 mg/kg to 1 mg/kg for a single dose. An effective amount of ensifentrine may be a dose of from about 0.1 mg to about 500 mg, or from about 0.1 mg to 100 mg, or from about 0.1 mg to about 6 mg. A single dose of ensifentrine may be from 0.3 mg to 3 mg.

An effective amount of glycopyrrolate is typically from about 0.001 mg/kg to 25 mg/kg for a single dose, for instance from 0.001 mg/kg to 0.5 mg/kg for a single dose. An effective amount of glycopyrrolate may be a dose of from about 0.01 mg to about 250 mg, or from about 0.02 mg to 3 mg. A single dose of glycopyrrolate may be from 0.02 mg to 2.0 mg.

The liquid pharmaceutical composition may be administered once, twice or three times a day, or may be administered twice, three times, four times or five times a week. For instance, the pharmaceutical composition may be administered twice a day.

The invention also provides use of a liquid pharmaceutical composition as defined herein in the manufacture of a medicament for the treatment of a disease or condition as defined herein.

The invention is described in more detail by the following Examples.

Examples

Methods

Assay and related substances testing were performed using high performance liquid chromatography with an acetonitrile:water mobile phase.

Example 1— Preparation of Formulations

Five pharmaceutical formulations (formulations A to E) comprising ensifentrine and glycopyrronium bromide (GP) were prepared.

The composition of the five formulations are shown in Table 1.

TABLE 1

| | Formulation | | | | |
|---|---|---|---|---|---|
| Component (mg/mL) | A | B | C | D | E |
| ensifentrine (suspension of particles) | 1.5 | 1.5 | 1.5 | 1.5 | 1.5 |
| glycopyrronium bromide (dissolved) | 0.15 | 1.5 | 15.0 | 0.15 | 15.0 |
| polysorbate 20 (Tween 20) | 0.5 | 0.5 | 0.5 | 0.5 | 0.5 |
| sorbitan monolaurate (Span 20) | 0.05 | 0.05 | 0.05 | — | — |
| monosodium phosphate monohydrate | 6.58 | 6.58 | 6.58 | — | — |
| dibasic sodium phosphate anhydrous | 6.80 | 6.80 | 6.80 | — | — |
| citric acid monohydrate | — | — | — | 9.9 | 9.9 |
| trisodium citrate dihydrate | — | — | — | 15.6 | 15.6 |
| sodium chloride | 4.80 | 4.80 | 4.80 | 9.0 | 9.0 |
| water | to 1 mL | to 1 mL | to 1 mL | to 1 mL | to 1 mL |
| ensifentrine:GP weight ratio | 10:1 | 1:1 | 1:10 | 10:1 | 1:10 |
| pH | 6.7 | 6.7 | 6.7 | 4.5 | 4.5 |

In each case, a suspension of particles of ensifentrine was first prepared at a concentration of 1.5 mg/mL in one of two vehicles:

(i) an aqueous solution of polysorbate 20, sorbitan monolaurate, monosodium phosphate monohydrate, dibasic sodium phosphate anhydrous and sodium chloride for formulations A to C; or (ii) an aqueous solution of polysorbate 20, citric acid monohydrate, trisodium citrate dihydrate and sodium chloride for formulations D and E.

Glycopyrronium bromide was then dissolved in the ensifentrine suspension at the stated concentration (0.15 mg/mL, 1.5 mg/mL or 15.0 mg/mL). The resulting formulations had the appearance of pale yellow suspensions which were free from visible agglomerates following re-suspension.

The pH of formulations A to C was determined to be 6.7. The pH of formulations D and E was determined to be 4.5.

Example 2— Stability of Formulations

The stability of formulations A to E with respect to chemical degradation of the active ingredients was assessed. 5 mL samples of the formulations were stored in stoppered glass vials under three different conditions: (a) 25° C./60% relative humidity (RH); (b) 40° C./75% RH; and (c) 60° C. All formulations were tested after storage under these conditions for two weeks. Formulations D and E were further tested after storage under these conditions for three months.

The results of the stability assessment after two weeks is set out in Table 2.

TABLE 2

| | Storage conditions (two weeks) | | |
|---|---|---|---|
| Formulation | 25° C./60% RH | 40° C./75% RH | 60° C. |
| A | GP degradation observed | GP degradation observed | GP degradation observed |
| B | GP degradation observed | GP degradation observed | GP degradation observed |
| C | GP degradation observed | GP degradation observed | Very significant GP degradation observed |
| D | No degradation observed | No degradation observed | Slight GP degradation observed |
| E | Slight GP degradation observed | Some GP degradation observed | GP degradation observed |

It can be seen that the pH 6.7 phosphate buffered formulations (A, B and C) were unstable under all conditions after two weeks with degradation of glycopyrronium observed. Formulation C after storage at 60° C. had significantly degraded and the particles of ensifentrine could not be re-suspended even after vigorous shaking.

In contrast, formulations D and E (pH 4.5 citrate buffered formulations) were more stable after two weeks than formulations A to C. No degradation was observed for formulation D after storage 25° C./60% RH or 40° C./75% RH. Slight degradation of the glycopyrronium was observed for formulation D after storage at 60° C.

There was some low level degradation of glycopyrronium observed for formulation E after storage 25° C./60% RH or 40° C./75% RH and more significant degradation after storage at 60° C.

In view of the instability of formulations A to C, no further stability assessment of those formulations was conducted. The stability of formulations D and E was assessed again at 3 months and the results are shown in Table 3.

TABLE 3

| | Storage conditions (three months) | | |
|---|---|---|---|
| Formulation | 25° C./60% RH | 40° C./75% RH | 60° C. |
| D | No degradation observed | No degradation observed | Slight GP degradation observed |
| E | Some GP degradation observed | GP degradation observed | GP degradation observed |

It was found that formulation D was stable after storage for 3 months at both 25° C./60% RH and 40° C./75% RH. Slight degradation of glycopyrronium was observed after storage at 60° C. for 3 months.

Some chemical degradation was observed after storage of formulation E for 3 months at 25° C./60% RH. More significant degradation was observed after storage for 3 months at 40° C./75% RH and 60° C.

CONCLUSION

Out of the five formulations tested, it has been observed that only formula D has suitable stability characteristics after storage. The inventors have accordingly found that a low pH and low glycopyrrolate concentration relative to the ensifentrine concentration are important for stable formulation of the combination of glycopyrrolate and ensifentrine for use as an inhaled product.

The invention claimed is:

1. A liquid pharmaceutical composition suitable for administration by inhalation comprising:

(i) ensifentrine particles;

(ii) glycopyrrolate; and (iii) a diluent, which diluent comprises water, wherein:

the concentration of ensifentrine particles is from 0.1 to 2.5 mg/ml;

the glycopyrrolate is dissolved in the diluent;

the concentration of glycopyrrolate is less than or equal to 0.25 mg/ml;

the pH of the liquid pharmaceutical composition is from 4.2 to 4.7; and the weight ratio of ensifentrine: glycopyrrolate in the liquid pharmaceutical composition is from 5:1 to 150:1.

2. The liquid pharmaceutical composition according to claim 1, wherein the pH of the liquid pharmaceutical composition is from 4.3 to 4.7.

3. The liquid pharmaceutical composition according to claim 1, wherein the liquid pharmaceutical composition further comprises a buffer, optionally wherein the concentration of the buffer is from 10.0 to 40.0 mg/mL.

4. The liquid pharmaceutical composition according to claim 1, wherein:

the concentration of glycopyrrolate is from 0.01 mg/mL to 0.25 mg/mL; and/or the weight ratio of ensifentrine: glycopyrrolate in the liquid pharmaceutical composition is from 8:1 to 120:1; and/or the concentration of ensifentrine particles is from 0.15 to 2.5 mg/mL; and/or the ensifentrine particles have a Dv50 of from 0.5 to 5.0 μm.

5. The liquid pharmaceutical composition according to claim 1, wherein the glycopyrrolate is a pharmaceutically acceptable salt of glycopyrronium.

6. The liquid pharmaceutical composition according to claim 1, wherein the diluent is water and the liquid pharmaceutical composition comprises at least 80% by weight of the diluent based on the total weight of the liquid pharmaceutical composition; and/or the liquid pharmaceutical composition further comprises a tonicity adjuster, optionally wherein the concentration of the tonicity adjuster is greater than or equal to 1.0 mg/mL.

7. The liquid pharmaceutical composition according to claim 1, wherein the liquid pharmaceutical composition further comprises one or more surfactants, optionally wherein the total concentration of the one or more surfactants is from 0.01 to 2.0 mg/mL.

8. The liquid pharmaceutical composition according to claim 1, wherein the liquid pharmaceutical composition comprises:

(i) ensifentrine particles;
(ii) glycopyrrolate;
(iii) the diluent;
(iv) a polysorbate surfactant;
(v) optionally a sorbitan alkyl ester surfactant;
(vi) a citrate buffer; and
(vii) sodium chloride.

9. The liquid pharmaceutical composition according to claim 1, wherein the liquid pharmaceutical composition comprises:

(i) from 0.1 to 2.5 mg/mL ensifentrine particles;
(ii) from 0.01 mg/mL to 0.25 mg/mL glycopyrronium bromide;
(iii) water;
(iv) from 0.1 to 1.0 mg/mL polysorbate 20;
(v) optionally from 0.01 to 0.1 mg/mL sorbitan monolaurate;
(vi) from 5.0 to 15.0 mg/mL citric acid;
(vii) from 10.0 to 20.0 mg/mL trisodium citrate; and
(viii) from 5.0 to 15.0 mg/mL sodium chloride.

10. The liquid pharmaceutical composition according to claim 1, which liquid pharmaceutical composition is suitable for administration by a nebuliser.

11. A nebuliser comprising a liquid pharmaceutical composition according to claim 1.

12. The liquid pharmaceutical composition according to claim 3, wherein the buffer is a citrate buffer.

13. The liquid pharmaceutical composition according to claim 4, wherein the concentration of glycopyrrolate is from 0.01 mg/mL to 0.16 mg/mL.

14. The liquid pharmaceutical composition according to claim 4, wherein the weight ratio of ensifentrine: glycopyrrolate in the liquid pharmaceutical composition is from 10:1 to 120:1.

15. The liquid pharmaceutical composition according to claim 5, wherein the glycopyrrolate is glycopyrronium bromide or glycopyrronium chloride.

16. The liquid pharmaceutical composition according to claim 6, wherein the tonicity adjuster is sodium chloride.

17. The liquid pharmaceutical composition according to claim 7, wherein the one or more surfactants are selected from a polysorbate or a sorbitan alkyl ester.

18. A method of treating or preventing a disease or condition selected from chronic obstructive pulmonary disease (COPD), asthma, allergic asthma, hay fever, allergic rhinitis, bronchitis, emphysema, bronchiectasis, adult respiratory distress syndrome (ARDS), steroid resistant asthma, severe asthma, paediatric asthma, cystic fibrosis, lung fibrosis, pulmonary fibrosis, interstitial lung disease, a skin disorder, atopic dermatitis, psoriasis, ocular inflammation, cerebral ischaemia, an inflammatory disease and an autoimmune disease, which method comprises administering to a subject an effective amount of the liquid pharmaceutical composition of claim 1.

19. The method of claim 18, wherein the disease or condition is chronic obstructive pulmonary disease (COPD).

20. The liquid pharmaceutical composition according to claim 1, wherein:

the concentration of ensifentrine particles is from 0.1 to 2.0 mg/mL; and the concentration of glycopyrrolate is from 0.01 to 0.25 mg/mL.

21. The liquid pharmaceutical composition according to claim 1, wherein:

the concentration of ensifentrine particles is from 1.0 to 2.0 mg/ml;

the concentration of glycopyrrolate is from 0.01 to 0.16 mg/mL;

the pH of the liquid pharmaceutical composition is about 4.5; and the weight ratio of ensifentrine: glycopyrrolate in the liquid pharmaceutical composition is from 8:1 to 120:1.

* * * * *